United States Patent [19]

Lodder et al.

[11] Patent Number: 4,882,493

[45] Date of Patent: Nov. 21, 1989

[54] SAMPLE HOLDERS OR REFLECTORS FOR INTACT CAPSULES AND TABLETS AND FOR LIQUID MICROCELLS FOR USE IN NEAR-INFRARED REFLECTANCE SPECTROPHOTOMETERS

[75] Inventors: Robert A. Lodder, Bloomington, Ind.; Gary M. Hietze, Bloomington, Ind.; Mark Selby, Victoria, Australia

[73] Assignee: Indiana University Foundation, Bloomington, Ind.

[21] Appl. No.: 165,751

[22] Filed: Mar. 9, 1988

[51] Int. Cl.[4] .................. G01N 21/84; G01N 21/01
[52] U.S. Cl. .................................. 250/353; 209/587; 250/339; 356/237; 356/244
[58] Field of Search ............... 250/353, 339; 356/244, 356/237; 209/587, 912

[56] References Cited

U.S. PATENT DOCUMENTS 3,757,943  9/1973  Chae et al. ........................ 209/551
4,143,770  3/1979  Grimmell et al. ................. 209/558

FOREIGN PATENT DOCUMENTS 1598426  9/1981  United Kingdom ............... 356/237

OTHER PUBLICATIONS

G. C. Sommer and B. H. Yun, "Detection and Measurement of Epitaxial Spikes," IBM Technical Disclosure Bulletin vol. 13, No. 11, (Apr. 1971) p. 3496 [U.S. Classification: 356/237].
J. A. Pesch, D. F. Solum and W. L. Zaker, "Goniometer," IBM Technical Disclosure Bulletin vol. 12, No. 1 (Jun. 1969), p. 42 [U.S. Classification: 356/244].
C. A. Watson, "Near Infrared Reflectance Spectrophotometric Analysis of Agricultrual Products," Anal. Chem. vol. 49, pp. 835A-840A (Aug. 1977).
E. W. Ciurczak et al., "Determination of particle Size of Pharmaceutical Raw Materials Using Near-Infrared Reflectance Spectroscopy," Spectroscopy vol. 1, No. 7, pp. 36-39 (Jul., 1986).
E. W. Ciurczak et al., "Identification of Actives in Multicomponent Pharmaceutical Dosage Forms Using Near-Infrared Reflectance Analysis," Spectroscopy vol. 1, No. 1, pp. 36-39 (Jan. 1986).
T. Hirschfeld, "Near Infrared Trace and Microanalysis," Paper No. 1093, Pittsburgh COnference, New Orleans, LA (Feb. 1985).
D. A. Burns, "Letter to the Editor," Spectroscopy, vol. 1, No. 3, p. 10 (Mar. 1986).
M. Fuller et al. Diffuse Reflectance measurements by Infrared Fourier Transform Spectroscopy, Nov. 1978, Anal. Chem. vol. 5, pp. 1906-10

Primary Examiner—Constantine Hannaher
Attorney, Agent, or Firm—Kirkland & Ellis

[57] ABSTRACT

The present invention relates to unique holders or reflectors for NIRS samples, in particular for tablets, capsules and liquids. These holders comprise a main body with a substantially 90° right-circular cone-shaped receptacle therein.

8 Claims, 4 Drawing Sheets

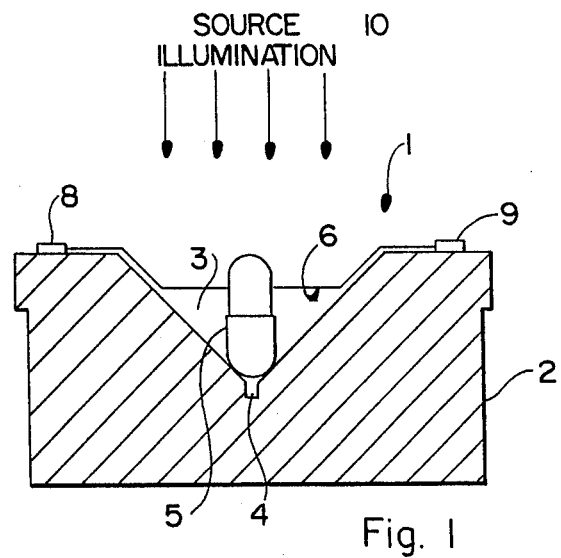
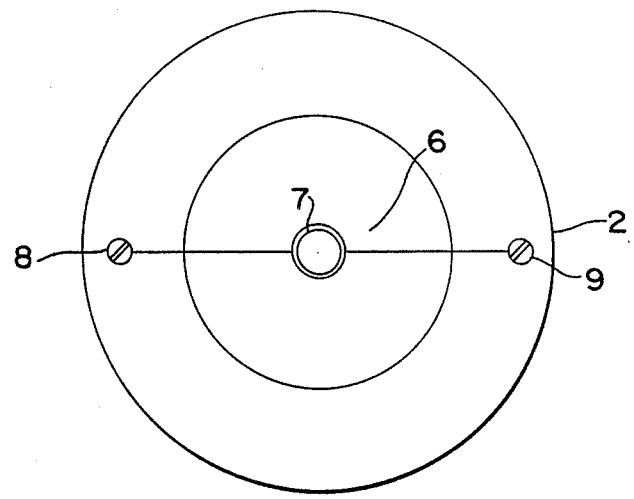
Fig. 1
Fig. 2

SAMPLE HOLDERS OR REFLECTORS FOR INTACT CAPSULES AND TABLETS AND FOR LIQUID MICROCELLS FOR USE IN NEAR-INFRARED REFLECTANCE SPECTROPHOTOMETERS

BACKGROUND OF THE INVENTION

Copending application Ser. No. 07/166,211 filed on Mar. 10, 1988, is incorporated herein by reference.

FIELD OF THE INVENTION

The present invention relates to sample holders or reflectors for use in near-infrared reflectance spectrophotometers.

PRIOR ART

Near-infrared reflectance spectroscopy ("NIRS"), often used for analyses of agricultural products, C.A. Watson, *Anal. Chem.* 49(9). 835A (1977), is now being used for analyses of pharmaceuticals as well. In recent reports, NIRS has been used to determine the particle sizes of pharmaceutical raw materials and to perform qualitative analyses of powdered product mixtures. E.W. Ciurczak, R.P. Torlini, and M.P. Demkowicz, *Spectroscopy* 1(7), 36 (1986); E.W. Ciurczak and T.A. Maldacker, *Spectroscopy* 1(1), 36 (1986).

In the past, it has been difficult, if not impossible to use NIRS to analyze typical pharmaceutical tablets and capsules. For example, an aspirin tablet is too small for analysis in an ordinary NIRS instrument because it weighs only about 400 milligrams and occupies a volume of about 250 microliters. A tablet the size of an aspirin would not begin to fill conventional solid-sample holders. In addition, capsules are difficult to analyze with NIRS because they have odd shapes and require unique positioning and support for analysis. Furthermore, most solid-sample holders are designed for powdered samples, requiring that the integrity of the tablets or capsules be destroyed and the resulting powders pooled before analysis may be accomplished with NIRS. Potential NIRS applications, and even routine quality control, such as the detection of product tampering, are unnecesearily complicated by this pooling and/or grinding requirement.

Focusing reflectors for small samples have been designed for use in NIRS instruments. To date, however, these reflectors have required grinding or pooling of the sample. T. Hirschfield, *Paper* 1093. presented at the Pittsburgh Conference, New Orleans, LA, Feb. 1985. Focusing reflectors also are problematical because many NIRS samples are inhomogeneous. Thus, if the incident radiation is focused on too small a spot, the probability of obtaining an unrepresentative result increases.

In addition to problems experienced in obtaining holders or reflectors for analyses of certain solid sample types, such as intact capsules and tablets, problems in obtaining holders to measure small liquid samples have been experienced as well. Most available liquid analysis holders or reflectors are cumbersome and expensive. A typical liquid holder or reflector requires that a relatively large volume of sample be used (on the order of milliliters) and that complex purge/fill and wash cycles be utilized to prevent clogging. If clogging does occur, cleaning can be difficult.

Accordingly, it is an object of present invention to provide a sample holder or reflector for small samples, such as pharmaceutical tablets, for analysis using NIRS.

It is another object of the present invention to provide a sample holder or reflector for capsules for analysis using NIRS.

It is a further object of the present invention to provide a sample holder or reflector which permits a sample, such as a tablet or capsule, to be analyzed using NIRS, without grinding or destroying the integrity of such a sample.

It is an additional object of the present invention to provide a holder or reflector for a liquid microcell for analysis using NIRS.

BRIEF DESCRIPTION OF THE DRAWINGS

FIG. 1 is a cross-sectional view of the preferred embodiment of the holder or reflector for capsules.

FIG. 2 is a top view of the preferred embodiment of the reflector or holder for capsules.

SUMMARY OF THE INVENTION

Figure 3:
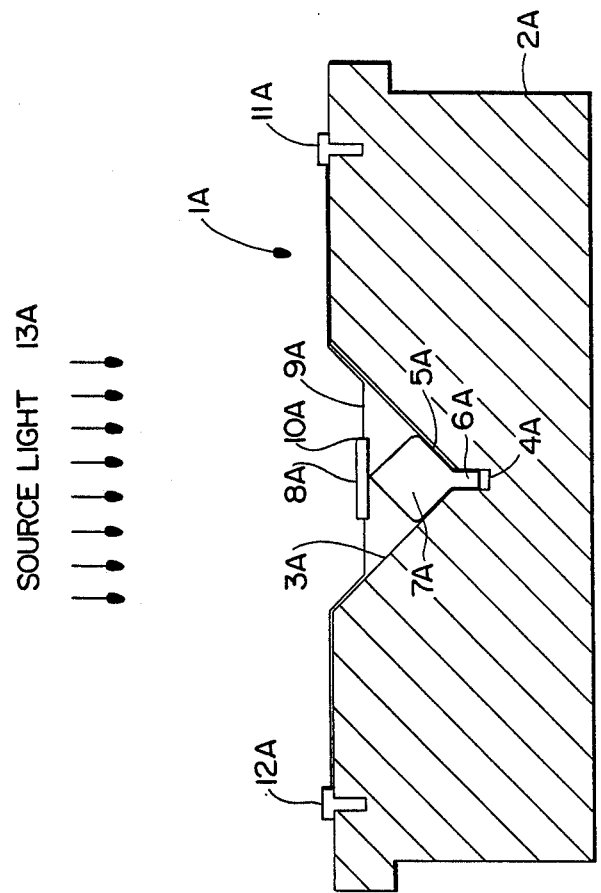
FIG. 3 is a cross-sectional view of a preferred embodiment of the holder or reflector for tablets.

The foregoing objects, advantages and features of the present invention may be achieved with NIRS holders or reflectors for pharmaceutical samples and liquids. The present invention is a holder for samples, such as tablets and capsules, and liquid samples, such as blood. The holder comprises a main body comprising a metal disc with polished substantially 90° right-circular cone-shaped receptacle therein. This main body is of a size and shape which fits into a sample holder drawer of a near-infrared reflectance spectrophotometer. The preferred embodiment for tablets also comprises a polished insert, comprising a cylindrical portion and a substantially right-circular 90° insert cone portion which is oriented in an opposing direction to the cone-shaped receptacle of the main body. The insert is inserted into the cone-shaped receptacle. The preferred embodiment for liquids also comprises an insert comprising a cylindrical portion and a substantially 135° insert cone portion which is oriented in an opposing direction to the cone-shaped receptacle. The holder for the tablets and capsules also comprises a wire for positioning and stabilizing a sample suspended above and across the cone-shaped receptacle of the main body, while the holder for liquids has a cavity slide and cover slip for holding a sample also suspended above and across the cone-shaped receptacle.

DETAILED DESCRIPTION OF THE INVENTION

A. Preferred Embodiment For Capsules

FIG. 1 shows a holder or reflector generally denoted by numeral 1. Holder 1 comprises main body 2, which comprises a metal disc with a substantially 90° right-circular polished cone-shaped receptacle 3 therein. Main body 2 should be constructed from a material which is reflective in the near-infrared region of the spectrum or plated with such a material. Gold-plating is preferred. In addition, if main body 2 is not plated, it preferably should be constructed from a single block of such material. Main body 2 is round and of a size and shape which fits into a solid-sample drawer of a near-infrared reflectance spectrophotometer, such as an InfraAlyzer 400 spectrophotometer. In addition, the dimensions of main body 2 must comport with the diameter of the incident beam of the near-infrared reflectance spectrophotometer.

A second smaller hole or receptacle 4 of a small diameter may be located at the vertex of cone-shaped receptacle 3, but is not required for this embodiment. A capsule 5 is secured in cone-shaped receptacle 3 of main 2 body by a wire 6 which is suspended above and across said cone-shaped receptacle 3. Wire 6 forms a loop 7 directly above the center of cone-shaped receptacle 3 of main body 2 and is for holding and stabilizing capsule 5. A cylindrical quartz sample holder with a cavity therein also, may be placed in loop 7 for the purpose of holding and stabilizing capsule 5. As more fully shown in FIG. 2, wire 6 may be secured at opposing sides of main body 2, preferably by screws 8 and 9. Capsule 5, also, may be positioned and secured in cone-shaped receptacle 3 by means other than wire 7, such as by a container made from quartz, glass or diamond which is capable of fitting directly into cone-shaped receptacle 3. Other means also may be used.

This holder or reflector is especially configured to reduce specular reflectance. When empty, holder or reflector 1 reflects radiation back toward a source 10, parallel to the incident beam of that source. When capsule 5 is positioned along the axis of rotation of main body 2, the specular reflectance can be minimized while the diffuse reflectance is maximized. Radiation reflected from the surface of capsule 5 is returned to source 10 when the incident radiation is perpendicular to the base of main body 2—this is the configuration used in most spectrophotometers. Radiation is then focused along the length of capsule 5. Any radiation that might pass through capsule 5 without being scattered is also returned to source 10. Therefore, the bulk of the radiation which reaches a detector on a NIRS instrument is radiation scattered by the contents of capsule 5.

If the base of main body 2 is uniformly illuminated by collimated radiation (as is the case with most spectrophotometers), the amount of radiation incident on any given segment of capsule 5 is directly proportional to the curved surface area of a frustum (a conic section taken parallel to the base of cone-shaped receptacle 3 of main body 2) in which it lies. In turn, the frustum near the vertex of cone-shaped receptacle 3 and the frustum near the base of the same cone-shaped receptacle do not have the same curved surface area. (The curved surface area of a frustum is given by $\pi s(r_1 + r_2)$, where $r_1$ and $r_2$ are the radii of the base and top of a right-circular frustum, respectively, and s is the length of the generator line, i.e., the length between the top and bottom measured along the surface of cone-shaped receptacle 3).

For example if the length of capsule 5 is divided into 1 millimeter segments and these segments are numbered from 1 to 20, starting at the end of capsule 5, i.e., toward the vertex of cone-shaped receptacle 3, the top segment of the capsule (i.e.. segment no. 20) will receive 39 times more light than the bottom segment (i.e., segment 1). In fact, the amount of light (P) received by a particular segment numbered R (the height of the section above the inverted vertex of cone shape receptacle 3) is given by:

$$P = k(2\pi\sqrt{2})R - \pi\sqrt{2} \qquad (1)$$

Because each 1 millimeter section of capsule 5 does not have a separate detector in the NIRS instrument, the detector inside the integrating sphere of the NIRS instrument integrates the signal from the entire capsule to produce the detector response:

$$\text{detector response} = k'(\pi\sqrt{2})R'^2 - (\pi\sqrt{2}R'), \qquad (2)$$

where k and k' are proportionality constants that depend principally on the amount of incident radiation and the nature of the material in the capsule, and R' is the total number of vertical capsule segments filled (i.e., from R=1 to R').

The diameter of the incident beam of an InfraAlyzer 400 spectrophotometer, for example, is 26 millimeters. Such a proportionment causes direct illumination of the upper segments of capsule 5 (i.e., R=13 to 20) by the incident beam to be the predominant factor in producing a signal from this region. The amount of light on each segment decreases exponentially as the segment number is decreased in this zone. Of course, the entire cone-shaped receptacle 3 is filled with scattered light, and the thickness and composition of the wall of capsule 5 are not uniform over the capsule length. These two factors, combined with the probable sample inhomogeneity, prevent a simple analysis from completely explaining the signal observed from an individual capsule. The overall response, however, follows the trends outlined above.

B. Preferred Embodiment For Tablets

FIG. 3 shows a sample holder or reflector for small samples such as tablets, which is generally denoted by numeral 1A. The holder has a main body 2A comprising a metal disc with a substantially 90° right-circular polished cone-shaped receptacle 3A therein. Main body 2A should be constructed from a material which is reflective in the near-infrared region of the spectrum or be plated with such a material. Gold-plating is preferred. In addition, if main body 2A is not plated, it preferably should be constructed from a single block of such material. Main body 2A is round and fits into a solid-sample drawer of a spectrophotometer, such as an InfraAlyzer 400 spectrophotometer, in place of the conventional closed sample cup. In addition, the dimensions of main body 2A must comport with the diameter of the incident beam of a near-infrared reflectance spectrophotometer.

A second smaller diameter receptacle 4A, preferably 2 millimeters in diameter, is located at the vertex of cone-shaped receptacle 3A in main body 2A and serves to receive and stabilize an insert 5A. Insert 5A comprises a cylindrical portion 6A, which may be inserted into second receptacle 4A, and a substantially 90° right-circular polished insert cone portion 7A. Insert 5A preferably should be constructed from a material which is reflective in the near-infrared region of the spectrum or plated with such a material. Gold-plating is preferred. Oriented in an opposing direction to cone-shaped receptacle 3A of main body 2A, insert cone portion 7A directs light passing around a sample tablet 8A up underneath the tablet. Tablet 8A is suspended above and across cone-shaped receptacle 3A on a wire 9A, containing a loop 10A for holding and securing tablet 8A directly above insert 5A. A cylindrical quartz holder with a cavity therein also may be placed in loop 10A to hold tablet 8A. Wire 9A preferably should be made from a sturdy metal wire and be gold-plated and is preferably 8 millimeters in diameter. Wire 9A is attached to main body 2A at opposing sides of main body 2A, preferably by screws 11A and 12A. Tablet 8A also may be positioned and secured in cone-shaped receptacle 3A by means other than wire 9A, such as by a container made from quartz, glass or diamond which is capable of fitting directly int cone-shaped receptacle 3A. Other means also may be used.

The bottom of tablet 8A is illuminated by a double reflection. First, collimated light from a light source 13A is directed perpendicularly onto holder 1A and reflected off main body 2A. Second, reflections from insert cone portion 7A of insert 5A recollimate the light back in the direction of light source 13A. At this point the light is intercepted by sample tablet 8A and scattered into the integrating sphere and the detector of a NIRS instrument. The preferred embodiment of the present invention for tablets operates in the same manner as that of the preferred embodiment for capsules.

C. The Preferred Embodiment For Liquid Microcells

Figure 4:
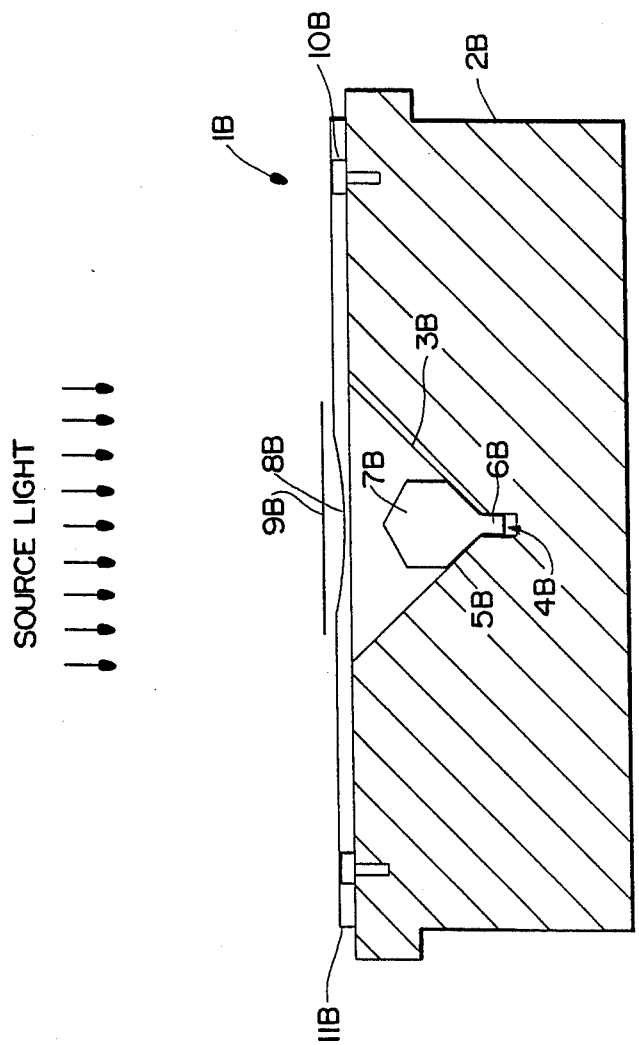
FIG. 4 is a cross-sectional view of the preferred embodiment of the holder or reflector for liquid microcells.

FIG. 4 shows a holder or reflector for a liquid microcell, generally denoted by numeral 1B, for use in a near-infrared reflectance spectrophotometer, such as a Technicon InfraAlyzer 400. Liquid microcell holder 1B comprises a main body 2B comprising a metal disc with a substantially 90° right-circular cone-shaped receptacle 3B therein. Cone-shaped receptacle 3B preferably has a height and a base radius of 13 millimeters, however, other dimensions may be satisfactory. Main body 2B should be constructed from a material which is reflective in the near-infrared region of the spectrum or plated with such material. Gold-plating is preferable. In addition, if main body 2B is not plated, it preferably should be constructed from a single block of such material. Main body 2B is of a size and shape which fits into the solid-sample drawer of a near-infrared reflectance spectrophotometer in place of the standard closed sample cup. In addition, the dimensions of main body 2B must comport with the diameter of the incident beam of the near-infrared reflectance spectrophotometer.

A smaller second receptacle 4B is located at the vertex of cone-shaped receptacle 3B in main body 2B and serves to stabilize an insert 5B. Insert 5B comprises a cylindrical portion 6B, which may be inserted into second receptacle 4B, and a substantially 135° insert cone portion 7B. Insert cone portion 7B is oriented in the opposing direction to that of cone-shaped receptacle 3B of main body 2B and preferably has a vertex of 135°. Insert 5B preferably should be constructed from a material which is reflective in the near-infrared region of the spectrum or plated with such a material. Gold-plating is preferred.

A standard single-cavity microscope slide 8B with a cavity therein (preferably 25×76 millimeters) is centered with cover slip 9B (preferably 22×22 millimeters) over cone-shaped receptacle 3B. The position of slide 8B may be made stable and reproduoible by resting it against screws 10B and 11B fastened onto main body 2B, screws 10B and 11B preferably being placed at either end of slide 8B.

The use of cavity slide 8B in the present invention has some distinct advantages over a conventional flat microscope slide: (1) it provides a longer and more reproducible optical pathlength, (2) cover slip 9B acts as a lid on the cavity in cavity slide 8B and lowers the liquid-sample evaporation rate, and (3) the cavity shape acts as a lens to scatter transmitted light into the integrating sphere of a near-infrared reflectance spectrophotometer. When completely filled with a liquid cell sample single-cavity slide 8B (which can be obtained from Dickinson and Company, Parsippany, NJ, #3720) and an ordinary cover slip 9B ( which can be obtained from American Scientific Products, McGaW Fark, 1L, #M6045-2) can contain from about 70 to 110 microliters of sample. However, different slides and cover slips with different masses can be used to vary the optical pathlength and the sample cell volume. Cover slip 9B actually floats on the sample, while heavier cover slips tend to squeeze the sample and reduce the cell volume.

Insert cone portion 7B returns collimated light that passes through slide 8B, back through slide 8B and parallel to the walls of cone-shaped receptacle 3B. This design allows the bulk of the light that passes through the liquid in the cavity to be reflected directly into the instrument's integrating sphere at a 45° angle from the source light. In this design the 135° insert cone 7B portion of insert 5B is placed atop a small cylinder because the sample is actually below the integrating sphere; if insert cone portion 7B were to be lowered to the bottom (vertex end) of cone-shaped receptacle 3B much of the reflected light would miss the window of the integrating sphere.

Applications of the Licuid Microcell Embodiment

In the initial tests of this liquid cell holder or reflector, a set of aqueous sodium chloride solutions was run. The determination of sodium chloride in water can be difficult for several reasons. These reasons include: (1) that sodium chloride has no absorption bands in the near-infrared; (2) that water has very strong absorption bands in the near-infrared; and (3) that these water absorption bands are very temperature-dependent. Nevertheless, successful determinations of aqueous sodium chloride in concentrations from 30–38 grams per liter have been reported by using four wavelengths selected in a standard multiple linear regression procedure.

Twenty aqueous solutions of reagent-grade sodium chloride (ten for the training set and ten for the validation set) were prepared for analysis in the new liquid cell. Solutions ranged in concentration from 5 to 38 grams per liter. Each solution was loaded into a single-cavity slide two times, and four spectra were taken from each sample loading. Spectra were recorded at 16 wavelengths and the data were transformed to their principal axes to avoid the need for a time-consuming all-possible-combinations of wavelengths regression. In order to demonstrate that one need not be very particular about the initial selection of analytical wavelengths, the wavelength data near water absorption peaks were deliberately deleted from the recorded spectra (which contained data from 19 wavelengths). This also shows that relatively complex instruments, utilizing scanning monochromators to collect data at hundreds of wavelengths, are often unnecessary in NIRS.

Figure 5:
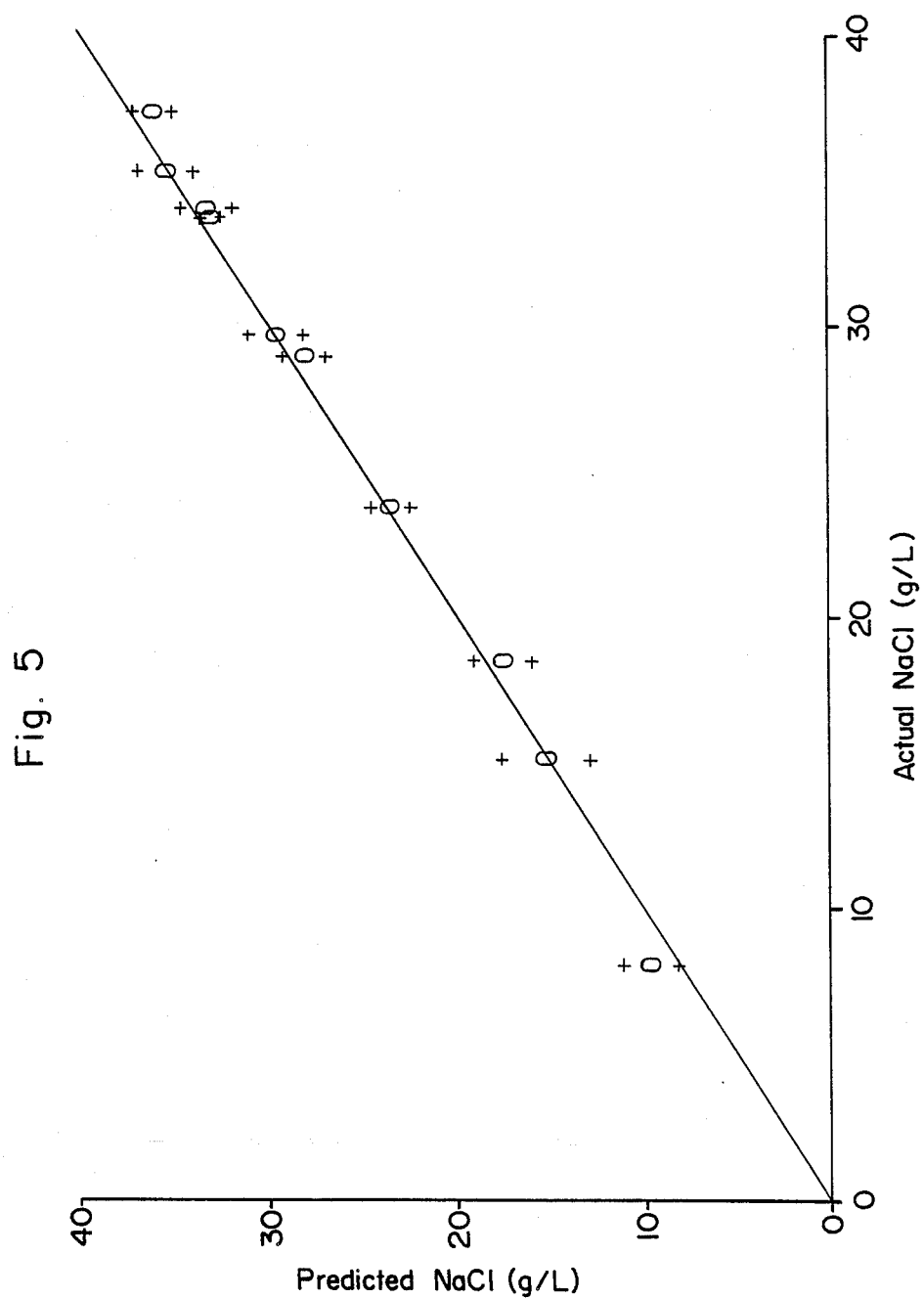
FIG. 5 is the near-infrared calibration for sodium chloride in water, obtained with the preferred embodiment for liquids.

Multiple linear regression was then carried out on the 80 training spectra using only the data along the first five principal axes (these axes accounted for over 99.9% of the total spectral variation). Data from five axes were required because evaporative loss from the cell produced pathlength variations that called for an additional degree of freedom in the system. The results of the training process are summarized in the calibration line in FIG. 5. The $r^2$ for the training set that produced the line is 0.97, and the r² value for the 80 validation spectra (shown superimposed on the calibration line, with error bars) is also 0.97. The detection limit for sodium chloride, calculated from both the error in the validation spectra and from four solvent blanks, is 1 gram per liter (1000 parts per million). This value corresponds to an absolute detection limit of approximately 100 micrograms in the 110 microliter sample cell.

The liquid microcell holder or reflector that has been described herein has a number of practical advantages It is faster and easier to use than an ordinary liquid holder. No heating or thermostatting is required because the volume of liquid used with this liquid micro cell holder rapidly reaches thermal equilibrium. No purging/filling or wash cycles are required. Any number of cells can be rapidly filled with a precision pipette if desired, and the cells can be easily cleaned or simply discarded afterward (an advantage for potentially dangerous and toxic samples). The configuration of the cell permits sensitive detection by enhancing transmission through the sample in a near-infrared reflectance instrument. The apparent lack of pathlength reproducibility for volatile samples is compensated simply by using a random selection of pathlengths when the training-set spectra are recorded and by letting the calibration process take care of the rest. This microcell design adds a versatility to liquid analysis in near-infrared reflectance instruments that complements the flexibility of the near-infrared calibration procedure.

While the foregoing has been described with respect to preferred embodiments and alternatives thereto, they are not intended nor should they be construed as limitations on the invention. As one skilled in the art would understand many variations and modifications of these embodiments may be made which fall within the spirit and scope of this invention.

What is claimed is:

1. A sample holder for use in an infrared spectrophotometer comprising:
   (a) a main body comprising a metal disc with a substantially 90° right-circular cone-shaped receptacle therein, said cone-shaped receptacle having a second smaller receptacle therein, located at the vertex of said cone-shaped receptacle:
   (b) an insert, which may be inserted into said cone-shaped receptacle, comprising a cylindrical portion, which may be inserted into said second receptacle, and a substantially 90° right-circular insert cone portion oriented in an opposing direction to the cone-shaped receptacle of said main body:
   (c) a wire, attached to said main body, which is suspended above and across said cone-shaped receptacle, said wire forming a loop directly above said insert cone portion for suspending a sample.

2. A sample holder as claimed in claim 1 wherein said wire is attached to said main body at opposing sides of said main bod by screws.

3. A sample holder for use in an infrared spectrophotometer comprising:
   (a) a main body comprising a metal disc with a substantially 90° right-circular cone-shaped receptacle therein, said cone-shaped receptacle having a second smaller receptacle therein, located at the vertex of said cone-shaped receptacle;
   (b) an insert, which may be inserted into said cone-shaped receptacle, comprising a cylindrical portion, which may be inserted into said second receptacle, and a substantially 90° right-circular insert cone portion oriented in an opposing direction to the cone-shaped receptacle of said main body.

4. A sample holder for use in an infrared spectrophotometer comprising:
   (a) a main body comprising a metal disc with a substantially 90° right-circular cone-shaped receptacle therein;
   (b) a wire attached to said main body, which is suspended above and across said cone-shaped receptacle, said wire forming a loop directly above said cone-shaped receptacle for suspending a sample.

5. A sample holder as claimed in claim 4 wherein said wire is attached to said main body at opposing sides of said main body by screws.

6. A sample holder for use in an infrared spectrophotometer comprising a main body comprising a metal disc with a substantially 90° right-circular cone-shaped receptacle therein.

7. A sample holder for use in an infrared spectrophotometer comprising:
   (a) a main body comprising a metal disc with a substantially 90° right-circular cone-shaped receptacle therein, said cone-shaped receptacle having a second smaller diameter receptacle therein, located at the vertex of said cone-shaped receptacle;
   (b) an insert, which may be inserted into said cone-shaped receptacle, comprising a cylindrical portion, which may be inserted into said second receptacle, and a substantially 135° insert cone portion, oriented in an opposing direction to said cone-shaped receptacle of said main body;
   (c) a cavity slide with a cavity therein which is suspended above and across said cone-shaped receptacle:
   (d) a cover slip positioned over the cavity of said cavity slide.

8. A sample holder for use in an infrared spectrophotometer as claimed in claim 7 wherein said cavity slide is secured to said main body by screws.

* * * * *

UNITED STATES PATENT AND TRADEMARK OFFICE
CERTIFICATE OF CORRECTION

Page 1 of 2

PATENT NO. : 4,882,493

DATED : November 21, 1989

INVENTOR(S) : Lodder et al.

It is certified that error appears in the above-identified patent and that said Letters Patent is hereby corrected as shown below:

```
Col. 1 line 10   ---211--- should be ---233---;
Col. 1 line 21   ---.--- should be ---,---;
Col. 1 line 51   ---.[third appearance]---should be ---,---;
Col. 2 line 41   ---a--- should be deleted;
Col. 3 line 58   insert ---,---after ---example---;
Col. 3 line 62   ---.[third appearance]--- should be ---,---;
Col. 5 line 9    insert ---o---after ---int---;
Col. 5 line 60   ---reproduoible--- should be ---reproducible---;
Col. 6 line 8    ---McGaW Fark, 1L--- should be ---McGaw Park,
                 IL---;
Col. 6 line 28   ---Licuid--- should be ---Liquid---;
Col. 7 line 5    ---I--- should be ---l---;
Col. 7 line 10   insert ---.--- after ---advantages---;
Col. 7 line 44   ---:--- should be ---;---;
Col. 7 line 50   ---:--- should be ---;---;
```

UNITED STATES PATENT AND TRADEMARK OFFICE
CERTIFICATE OF CORRECTION

Page 2 of 2

PATENT NO. : 4,882,493

DATED : November 21, 1989

INVENTOR(S) : Lodder et al

It is certified that error appears in the above-identified patent and that said Letters Patent is hereby corrected as shown below:

Col. 8 line 3 insert ---y--- after ---bod---; and
Col. 8 line 48 ---:--- should be ---;---.

Signed and Sealed this

Second Day of July, 1991

Attest:

Attesting Officer

HARRY F. MANBECK, JR.

Commissioner of Patents and Trademarks

UNITED STATES PATENT AND TRADEMARK OFFICE
CERTIFICATE OF CORRECTION

PATENT NO.  : 4,882,493

DATED       : November 21, 1989

INVENTOR(S) : Lodder et al.

It is certified that error appears in the above-identified patent and that said Letters Patent is hereby corrected as shown below:

ON THE TITLE PAGE:  Item [75]:

-- Hietze -- should be -- Hieftje --

Signed and Sealed this

Twenty-fourth Day of November, 1992

Attest:

DOUGLAS B. COMER

*Attesting Officer*     *Acting Commissioner of Patents and Trademarks*